(12) United States Patent
Rosenthal et al.

(10) Patent No.: US 6,524,274 B1
(45) Date of Patent: Feb. 25, 2003

(54) TRIGGERED RELEASE HYDROGEL DRUG DELIVERY SYSTEM

(75) Inventors: Arthur Rosenthal, Boston, MA (US); James J. Barry, Marlborough, MA (US); Ronald Sahatjian, Lexington, MA (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 08/478,745

(22) Filed: Jun. 7, 1995

Related U.S. Application Data (63) Continuation-in-part of application No. 08/240,292, filed on May 9, 1994, now abandoned, which is a continuation-in-part of application No. 07/796,402, filed on Nov. 22, 1991, now abandoned, which is a continuation of application No. 07/635,732, filed on Dec. 28, 1990, now abandoned.

(51) Int. Cl.[7] .................. A61M 29/00; A61M 25/00; A61M 31/00; A61N 17/20; B05D 3/00

(52) U.S. Cl. .................. 604/96.01; 604/265; 604/21; 604/509; 604/103.01; 604/103.02; 606/194; 600/435; 427/2.25

(58) Field of Search .................. 604/19, 27–28, 604/47–48, 500, 506–509, 514, 518, 522, 96.01, 103.01–103.02, 103.07–103.08, 113–114, 264–265, 523, 289–290; 606/191, 192, 194–195, 198; 600/433–435; 427/2.1, 2.22, 2.12–2.13, 2.24–2.25, 2.3

(56) References Cited

U.S. PATENT DOCUMENTS

| | | | |
|---|---|---|---|
| 4,299,226 A | 11/1981 | Banka | |
| 4,330,497 A | 5/1982 | Agdanowski | |
| 4,417,576 A | 11/1983 | Baran | |
| 4,423,725 A | 1/1984 | Baran et al. | |
| 4,448,195 A | 5/1984 | LeVeen et al. | |
| 4,515,593 A | 5/1985 | Norton | |
| 4,589,873 A | 5/1986 | Schwartz et al. | |

(List continued on next page.)

FOREIGN PATENT DOCUMENTS

| | | |
|---|---|---|
| EP | 0 372 088 | 6/1990 |
| EP | 0 379 156 | 7/1990 |
| EP | 0 399 712 | 11/1990 |
| SU | 1069826 | 1/1984 |
| WO | 91/05816 | 5/1991 |
| WO | 91/08790 | 6/1991 |
| WO | 92/13566 | 8/1992 |

OTHER PUBLICATIONS

Ilmain et al., "Volume Transition in a Gel Driven by Hydrogen Bonding", 1991, *Nature*, 349:400–401.

Irie et al. "Stimuli–responsive polymers: chemical induced reversible phase separation of an aqueous soution of poly(N–isopropylacrylamide) with pendent crown ether groups", 1993, *Polymer*, 34(21):4531–35.

(List continued on next page.)

*Primary Examiner*—Angela D. Sykes
*Assistant Examiner*—Patricia Bianco
(74) *Attorney, Agent, or Firm*—Kenyon & Kenyon

(57) ABSTRACT

The invention features a method for triggering release of a drug from a hydrogel polymer to tissue at a desired location of the body using a catheter. A portion of the catheter is coated on its outer surface with a polymer having the capacity to incorporate a predetermined substantial amount of drug which is immobilized in the polymer until released by a triggering agent or condition that is different from physiological conditions. Upon contact with a triggering agent or condition, the polymer reacts, e.g., swells or contracts, such that the drug is delivered to the desired body tissue. A balloon catheter is shown in which the hydrogel is carried on the exterior surface of the balloon.

16 Claims, 3 Drawing Sheets

U.S. PATENT DOCUMENTS

| | | | |
|---|---|---|---|
| 4,592,340 A | 6/1986 | Boyles | |
| 4,603,152 A | 7/1986 | Laurin et al. | |
| 4,693,243 A | 9/1987 | Buras | |
| 4,714,460 A | 12/1987 | Calderon | |
| 4,732,930 A | 3/1988 | Tanaka et al. | |
| 4,769,013 A | 9/1988 | Lorenz et al. | |
| 4,784,647 A | 11/1988 | Gross | |
| 4,799,479 A | 1/1989 | Spears | |
| 4,820,270 A | 4/1989 | Hardcastle et al. | |
| 4,832,688 A | 5/1989 | Sagae et al. | |
| 4,909,258 A | 3/1990 | Kuntz et al. | |
| 4,923,450 A | 5/1990 | Maeda et al. | |
| 4,983,166 A | 1/1991 | Yamawaki | |
| 4,993,412 A | 2/1991 | Murphy-Chutorian | |
| 4,994,033 A | 2/1991 | Shockey et al. | |
| 5,021,044 A | 6/1991 | Sharkawy | 604/53 |
| 5,041,100 A | 8/1991 | Rowland et al. | |
| 5,047,045 A | 9/1991 | Arney et al. | |
| 5,049,132 A | 9/1991 | Shaffer et al. | |
| 5,102,402 A | 4/1992 | Dror et al. | 604/265 |
| 5,120,322 A | 6/1992 | Davis et al. | 604/265 |
| 5,135,516 A | 8/1992 | Sahatjian et al. | 604/265 |
| 5,163,906 A | 11/1992 | Ahmadi | 604/101 |
| 5,180,366 A | 1/1993 | Woods | 604/96 |
| 5,226,430 A | 7/1993 | Spears et al. | 128/898 |
| 5,232,444 A | 8/1993 | Just et al. | 604/96 |
| 5,286,254 A | 2/1994 | Shapland et al. | |
| 5,304,121 A * | 4/1994 | Sahatjian | 604/103.02 |

OTHER PUBLICATIONS

Mamada et al., "Photoinduced Phase Transition of Gels", 1990, *Macromolecules*, 23:1517–19.

McMath et al., "Experimental Application of Bioprotective Materials to Injured Arterial Surfaces with Laser Balloon Angioplasty", *Circulation* (Supp. III) 82:0282 (abstract) (Oct. 1990).

Suzuki et al., "Phase Transition in Polymer Gels Induced by Visible Light", 1990, *Nature*, 346:345–47.

Tarcha, "Diffusion Controlled Systems: Hydrogels", *Polymers for Controlled Drug Delivery*, CRC Press, Inc., 1991, Ch. 2, pp. 15–37.

Tokuhiro et al., "NMR Study of Poly(N–isopropylaacrylamide) Gels near Phase Transition", 1991, *Macromolecules*, 24:2936–43.

Waller et al., "Vessel Wall Pathology After Angioplasty," *Cardio.* 57, 60, 69–72, 81 (Aug. 1990).

Waller et al., "Morphologic Observations Late after Coronary Balloon Angioplasty" Mechanisms of Acute Injury and Relationship to Restenosis, *Radio.* 174:961–967 (Mar. 1990).

Wolinsky et al., "Local Introduction of Drugs into the Arterial Wall: A Percutaneous Catheter Technique", *J. Interven. Cardiol.* 2:219–228 (1989).

* cited by examiner

TRIGGERED RELEASE HYDROGEL DRUG DELIVERY SYSTEM

This application is a Continuation-in-Part of application U.S. Ser. No. 08/240,292, titled Balloon Drug Delivery System, filed on May 9, 1994, now abandoned, which is a Continuation-in-Part of U.S. Ser. No. 07/796,402, titled Balloon Drug Delivery System, filed on Nov. 22, 1991, now abandoned, which in turn is a File Wrapper Continuation of application U.S. Ser. No. 07/635,732, titled Balloon Drug Delivery System, filed Dec. 28, 1990, now abandoned. The entire contents of these applications are hereby incorporated by reference.

FIELD OF THE INVENTION

The invention relates to delivery of drugs to a desired location within the body.

BACKGROUND OF THE INVENTION

Systemic administration of drugs treats the organism as a whole, even though the disease may be localized, such as occlusion of a duct or vessel. When administered to a patient systemically, many drugs, e.g., chemotherapeutic drugs such as those used to treat cancer and benign prostate hyperplasia, cause undesirable side effects. Localization of a drug poses special problems in cases involving the walls of ducts and vessels, since, by nature, these organs serve as transport systems.

Artherosclerotic disease, for example, causes localized occlusion of the blood vessels resulting from the build-up of plaque. As the deposits increase in size, they reduce the diameter of the arteries and impede blood circulation. Angioplasty, which involves the insertion of catheters, such as balloon catheters, through the occluded region of the blood vessel in order to expand it, has been used to treat artherosclerosis.

The aftermath of angioplasty in many cases is problematic, due to restenosis, or closing of the vessel, that can occur from causes including mechanical abrasion and the proliferation of smooth muscle cells stimulated by the angioplasty treatment. Restenosis may also occur as a result of clot formation following angioplasty, due to injury to the vessel wall which triggers the natural clot-forming reactions of the blood.

SUMMARY OF THE INVENTION

The invention features a method for delivering a drug to tissue at a desired location within the body comprising the following steps: providing a catheter constructed for insertion in the body, a portion of which carries a hydrogel having the capacity to incorporate a predetermined substantial amount of a drug which is substantially immobilized in the hydrogel until released by a triggering agent or condition that differs from ambient physiological conditions; introducing the catheter to the body to the point of desired drug application; and exposing the hydrogel to the triggering agent or condition. Exposure of the hydrogel to the triggering agent or condition triggers release of the drug from the hydrogel for delivery to the desired location within the body.

The invention also features a method for triggering release of a drug from a hydrogel to a tissue at a desired location of the body using a balloon catheter such as a non-vascular or vascular catheter, e.g., an angioplasty catheter. The balloon portion of the catheter is coated on its outer surface with a hydrogel having the capacity to incorporate a predetermined substantial amount of drug which is substantially immobilized in the hydrogel until released by a triggering agent or condition which is different from ambient physiological conditions. Preferably, the catheter has a porous balloon portion, e.g, a balloon with channels or pores through which a solution containing a triggering agent can pass and come in contact with the hydrogel. The invention also includes a kit for triggering release of a drug from a hydrogel-coated drug delivery catheter and a catheter for triggered drug delivery.

The method of triggered drug delivery includes the following steps: providing a catheter constructed for insertion in the body with a catheter shaft having an expandable hydrogel-coated porous balloon portion mounted on the catheter shaft which is expandable to engage the tissue at a controlled pressure to fill a cross-section of the body lumen and press against the body lumen wall; introducing the catheter to the body lumen wherein the balloon portion is positioned at the point of desired drug application; expanding the balloon portion to engage the tissue; and infusing the triggering agent into the hydrogel. Upon contact of the triggering agent with the hydrogel, the drug is released at the desired location of the wall of a body lumen.

Following release of the drug from the hydrogel coating, the hydrogel coating may be replenished with an additional dose of drug delivered to the hydrogel from the catheter through pores or channels in the porous balloon portion. The drug contacts the hydrogel and becomes immobilized in the hydrogel until a subsequent delivery of triggering agent to the hydrogel, which in turn, triggers release of the additional dose of drug. This process of replenishment of hydrogel with drug and triggered release may be repeated as many times as desired.

The drug to be delivered is associated with the hydrogel by covalent, ionic or hydrogen bonding. Preferably, the associations are ionic interactions, and the triggering agent increases local ionic strength causing release of the drug from the hydrogel. A change in ionic strength may also affect the hydrogel itself, causing a volume phase transition, e.g., an expansion or contraction, of the hydrogel, thus triggering release of the drug. The drug may also be associated with the hydrogel by hydrogen-bonding, and the drug released by a change in pH.

The drug may be cationic and the hydrogel anionic. Alternatively, the drug may be anionic and the hydrogel cationic. In either situation, release of the drug is induced by contacting the hydrogel with a physiologically-acceptable saline solution, the ionic strength of which differs from that of ambient physiological conditions. The saline solution alters the ionic strength in the microenvironment of the hydrogel, thus triggering drug release. Preferably, the solution consists essentially of 0.2M to 5 M NaCl, more preferably 0.2M to 3.5 M NaCl, and most preferably 0.1 to 0.2M NaCl. In addition to a physiologically-acceptable saline solution, any salt solution may be used to trigger drug release, e.g., sodium phosphate, sodium bicarbonate, sodium citrate, potassium chloride, sodium sulfate, or sodium acetate. The solution may also contain inactive ingredients, e.g., buffering agents or preservatives.

A variety of drugs may be delivered using the claimed methods. The drug may be an anti-thrombogenic drug, such as heparin; low molecular weight heparin, e.g., ENOXAPRIN; aspirin; phe-L-pro-L-arginyl chloromethyl ketone (PPACK); hirudin, HIRULOG®; Warfarin; Argatroban; or tissue factor pathway inhibitor (TPFI). The drug may also be a thrombolytic drug, such as urokinase; pro-urokinase;

streptokinase; tissue plasminogen activator; anisolated plasminogen streptokinase activator complex (APSAC), e.g., EMINASE®; an inhibitor of PAI-1, TA plasminogen; or cathepepsin D. Anti-platelet agents, such as chimeric 7E3 antibody (Reopro); Ticolpidine; Integrilin; TP9201; nitric oxide (NO) and derivatives thereof, e.g., protein-linked NO; Iloprost, or MK383, may be similarly delivered and triggered. Other drugs suitable for delivery in this manner include protein and polypeptide drugs, e.g., angiogenesis factors including but not limited to fibroblast growth factor (FGF), vascular endothelial growth factor (VEGF), transforming growth factor-beta, (TGFβ), platelet-derived growth factor (PDGF), epidermal growth factor (EGF), and urokinase. Other drugs to be delivered according to the invention include those to treat benign hyperplasia, e.g., PROSCAR®, and HYTRIN®. Other drugs include antiproliferative drugs, such monoclonal antibodies capable of blocking smooth muscle cell proliferation, e.g., anti-PDGF and anti-FGF; tyrosine kinase inhibitors, e.g., tyrophosphins, antisense oligonucletides to c-myc, c-myb; NO; gene encoding thymidine kinase (TK); fusion toxins, e.g, $DAB_{389}$-EGF; immunotoxins, angiopeptin; antioxidant drugs, e.g., probudol, lovastatin, vitamin C and vitamin E; calcium channel blockers, e.g., nificitine, veratimil, ACE inhibitors, fofinopril and cilazapril. Chemotherapeutic drugs to treat various forms of cancer, e.g., HLB-7; granulocyte macrophage colony stimulating factor (GM-CSF); interferonγ; immunotoxins, e.g., BMS-18224801, and BR-96-DOX; ONCOLYSIN®; fusion toxins, e.g., $DAB_{389}$-IL-2, and $DAB_{389}$-EGF; 5-Fluorouracil; methotrexate; and TAXOL®. The drugs may be in any form capable of associating with the hydrogel and subsequently being released from the hydrogel by a triggering agent, including small molecules, proteins, polypeptides, and DNA encoding such protein or polypeptide drugs.

The immobilized drug to be delivered to a body tissue may also be released from the hydrogel by contacting the hydrogel with a solution having a pH which induces a volume phase transition of hydrogel. pH-sensitive polymers include poly(hydroxethyl)methacrylate-co-methacrylic acid) and a copolymer of M,N,dimethylaminoethyl methacrylate and divinyl benzene. For example, the solution may cause the hydrogel to swell, thus allowing the drug to diffuse out of the hydrogel. Alternatively, the solution may cause the hydrogel to contract, thereby squeezing the drug out of the hydrogel. The pH of the triggering solution is slightly above or below, e.g., 0.1 pH unit greater than or less than ambient physiological pH, i.e., pH 7.4. For example, the pH of the solution is preferably greater than about 7.5., e.g., in the range of 7.5 to 8.4, or less than about 7.3, e.g., in the range of 6.4 to 7.3. The pH of the solution may also be slightly above or below the optimal pH of the drug/hydrogel interaction. In addition to inducing a volume phase transition of the hydrogel, a change in pH can also be used to trigger release of a drug associated with a hydrogel by hydrogen bonding.

The invention also includes a method of triggered drug delivery in which a balloon portion of a catheter is inflated to a pressure condition that triggers release of said drug from the hydrogel. Preferably, the pressure condition is at least two atmospheres.

The invention also features a method for triggering release of a drug from a temperature-sensitive hydrogel which includes the steps of: providing a thermal catheter constructed for insertion in a body lumen with a catheter shaft having an expandable balloon portion coated with a temperature-sensitive hydrogel previously loaded with the drug to be delivered; introducing the catheter to the body to the point of desired drug application; expanding the balloon portion to engage the tissue; and applying heat to the temperature-sensitive hydrogel. An increase in temperature above body temperature, e.g., at least 1° C. above ambient body temperature, triggers release of the drug at the desired location of the wall of a body lumen by inducing a volume phase transition of the hydrogel. In preferred embodiments, the temperature-sensitive hydrogel is a polyacrylic acid or derivative thereof, e.g., poly (N-isopropylacrylamide) gel, and the increase in temperature causes the hydrogel to contract, thereby forcing the drug out of the hydrogel. Alternatively, the temperature-sensitive hydrogel is an interpenetrating hydrogel network of poly(acrylamide) and poly (acrylic acid), and the increase in temperature causes the hydrogel to swell, thereby allowing the drug to diffuse out of the gel.

The temperature required for triggering release of the drug from the hydrogel is preferably between 1–80° C. above ambient body temperature, e.g., 37° C. More preferably, the temperature is between 1–50° C. above body temperature, and most preferably, the temperature is between 1–5° C. above body temperature, e.g. 38° C.

Drugs to be delivered and released by a temperature-sensitive hydrogel include anti-thrombogenic agents, thrombolytic agents, anti-proliferative agents, anti-platelet agents, and chemotherapeutic agents. The drugs may be in any form capable of associating with the hydrogel and subsequently being released from the hydrogel by a triggering agent, including proteins, polypeptides, and DNA encoding such protein or polypeptide drugs.

Also within the invention is a method for triggering release of a drug from a hydrogel which is responsive to a specific wavelength of electromagnetic radiation. Preferably, the electromagnetic radiation required to trigger drug release has a wavelength in the visible range or in the ultraviolet range.

The hydrogel may contain a photo-sensitive compound capable of mediating a charge transfer, e.g., a compound containing a porphyrin ring. In preferred embodiments, drug release is triggered by exposure of the hydrogel to visible light and the hydrogel contains the photo-sensitive compound, chlorophyllin, e.g., a copolymer of N-isopropylacrylamide and chlorophyllin, which upon exposure to a visible wavelength of light causes the polymer to contract thereby triggering release of the drug. A light-triggered hydrogel may also contain a photo-sensitive dye, e.g., rhodamine.

In another embodiment, drug release is triggered by ultraviolet light which causes the hydrogel to swell, thereby allowing the drug to diffuse out of the hydrogel. For example, the hydrogel may contain a UV-sensitive compound such as leucocyanide or leucohydroxide, and the photo-sensitive hydrogel may be a copolymer of N-isopropylacrylamide and bis (4-dimethylamino)phenyl) (4-vinylphenyl)methyl leucocyanide.

The method for triggering release of a drug from a hydrogel which is responsive to electromagnetic radiation includes the following steps: providing a catheter constructed for insertion in a body lumen with a catheter shaft having (1) an expandable balloon portion coated with a electromagnetic radiation-sensitive hydrogel in which a drug has been immobilized and (2) an electromagnetic radiation-emitting fiber, e.g., a fiber optic device; introducing the catheter to the body lumen, at the point of desired drug application; expanding the balloon portion to engage the tissue; and exposing the hydrogel-coated balloon portion to the electromagnetic radiation.

Also within the invention is a method for triggering release of a drug from a hydrogel to a tissue from a balloon catheter containing a double membrane balloon portion of the catheter. At least a portion of the exterior surface of the expandable portion of the catheter is covered with a porous membrane positioned over the surface of the balloon portion to create a space into which a triggering agent or an additional dose of drug is introduced. The porous membrane is coated on its outer surface with a hydrogel which has been loaded with the drug to be delivered. The drug is immobilized in the hydrogel until released by a triggering agent, and the porous membrane is constructed to transmit the triggering agent from the space through openings in the membrane to the outer surface of the membrane in response to pressure applied by inflation of the balloon portion to compress the space. The space may be loaded with triggering agent. After the triggering agent has been delivered to the hydrogel and the drug released, the space may be re-filled with an additional dose of drug which, upon compression out of the space, contacts the hydrogel and replenishes it for the next triggered release.

Triggering drug-release from a drug-laden hydrogel using a double membrane balloon catheter includes the following steps: providing a catheter constructed for insertion in a body lumen having a catheter shaft with an expandable balloon portion and a porous membrane coated with a drug-containing hydrogel covering at least a portion of the balloon portion creating a space between the two membranes; preparing the balloon portion by introducing the triggering agent into the space; introducing the catheter to the body lumen at the point of desired drug application; and expanding the balloon portion to enable delivery of the triggering agent to the hydrogel by compression of the space.

To replenish the hydrogel coating with drug after a previous dose drug was released, the method requires the additional steps of: deflating the balloon portion after the expanding step; introducing into the space a solution of drug;, inflating the balloon portion to enable replenishment of the hydrogel with drug by squeezing the drug out of the space and into the hydrogel where the drug becomes immobilized until contacted with the triggering agent; and repeating the preparing and expanding steps.

In preferred embodiments, the drug is associated with the hydrogel by an ionic interaction, and the triggering agent, e.g., physiologic saline, optimally containing 0.1 to 0.2 M NaCl, increases the local ionic strength causing release of the drug from the hydrogel. The triggering agent administered to the hydrogel may also be a solution with a pH that induces a volume phase transition in the hydrogel, e.g., an expansion or contraction of the hydrogel, thereby triggering release of said drug. Altering the pH of the microenvironment of the hydrogel may also disrupt hydrogen bonds between the drug and the hydrogel, thus releasing the drug from the hydrogel. The pH of the solution is preferably greater than or equal to 7.5 and less than or equal to 7.3.

Other features and advantages of the invention will be apparent from the following description of the preferred embodiments thereof, and from the claims.

DESCRIPTION OF PREFERRED EMBODIMENTS

We first briefly describe the drawings.

DRAWINGS

FIGS. 7a and 7b are further enlarged schematic illustrations of a portion of FIG. 7 and show the manner in which a semi-permeable balloon prevents passage (FIG. 7a) and enables passage (FIG. 7b) of a drug, while

GENERAL DESCRIPTION

Figure 1:
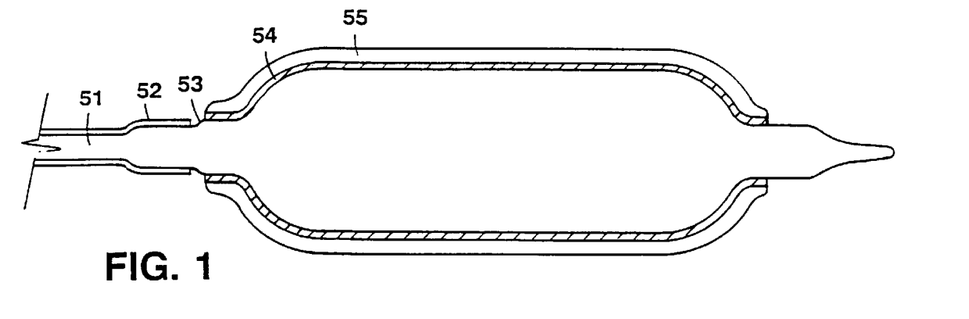
FIG. 1 is a cross sectional view of a drug delivery balloon catheter equipped with an aperture upstream (relative to blood flow) of the balloon through which a solution can pass to contact a hydrogel coating on the outside of the balloon.

As shown in FIG. 1, a solution containing a triggering agent is delivered to the hydrogel 55 on the outer surface of the balloon portion 54 of a drug delivery catheter 51 via a lumen 52 of the catheter 51. The solution passes to the outside of the balloon portion 54 through an aperture 53 which is located upstream (with respect to the flow of bodily fluids, e.g., blood) of the balloon portion 54. The solution is then carried by the flow of bodily fluids toward the balloon portion 54 where the solution washes over the hydrogel 55. Contact of the triggering agent with the hydrogel 55 induces the release of drug carried by the hydrogel.

Figure 2:
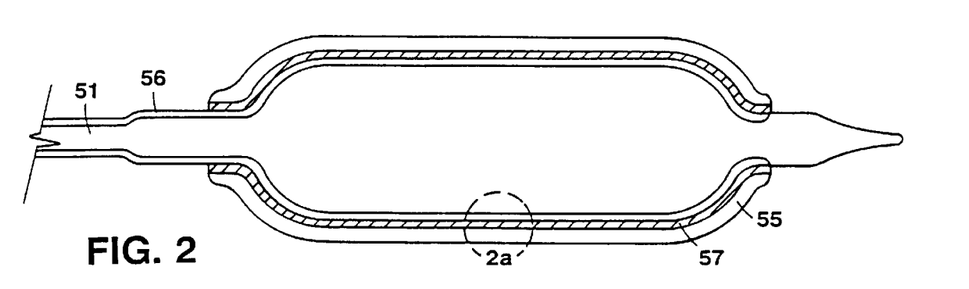
FIG. 2 is a cross sectional view of a drug delivery balloon catheter in which the balloon portion of the catheter has pores or channels through which a solution can pass to contact a hydrogel coating on the outside of the balloon.
Figure 2A:
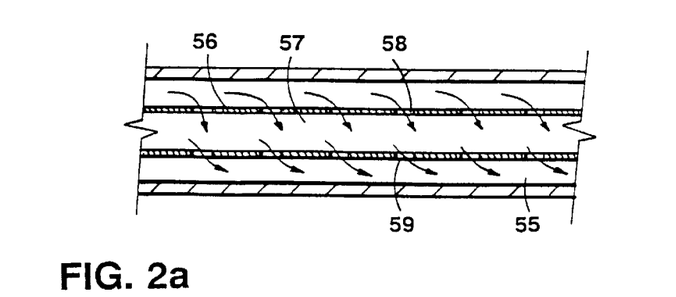
FIG. 2a is an enlarged cross sectional view of the balloon portion of a drug delivery balloon of FIG. 2 showing pores through which a solution can pass to contact a hydrogel coating on the outside of the balloon

As shown in FIG. 2, a solution containing a triggering agent is delivered to the hydrogel 55 through lumen 56 which contacts a porous balloon portion 57. Referring to FIG. 2a, the solution delivered through the lumen 56 exits the lumen 56 through a lumen aperture 58 and enters the porous balloon portion 57. The solution migrates through the porous balloon portion 57, exiting the porous balloon portion 57 through a balloon aperture 59 and entering the hydrogel 55. In the absence of lumen 56, a solution containing a triggering agent can pass directly to the hydrogel 55 through the catheter 51.

Figure 3:
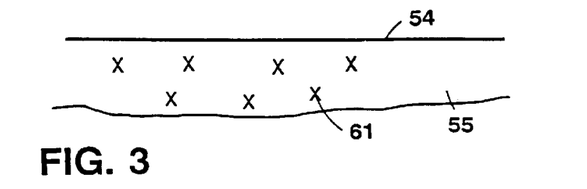
FIG. 3 is an enlarged cross sectional view of a drug-containing hydrogel coating on the outside surface of a drug delivery catheter.
Figure 4:
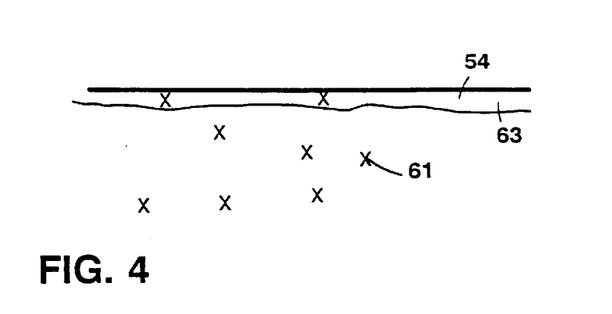
FIG. 4 is an enlarged cross sectional view of a contracted hydrogel on the outside surface of a drug delivery catheter.

As shown in FIG. 3, a drug 61 is carried in or on the hydrogel 55 coating the outside of the balloon portion 54 of the catheter 51. When the hydrogel is exposed to an appropriate triggering agent, e.g., solution containing a triggering agent, or triggering condition, e.g., heat or light, the hydrogel contracts as shown in FIG. 4. The drug 61 is then squeezed out of the contracted hydrogel 63.

Figure 5:
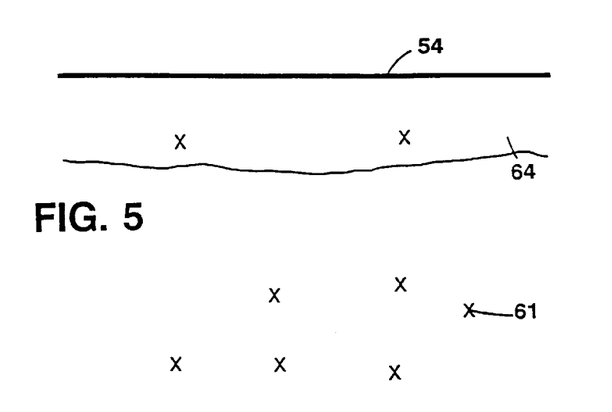
FIG. 5 is an enlarged cross sectional view of an expanded hydrogel on the outside surface of a drug delivery catheter.

As shown in FIG. 5, the hydrogel 55 expands when exposed to an appropriate triggering agent or condition. The drug 61 then diffuses out of the expanded hydrogel 64.

Figure 6:
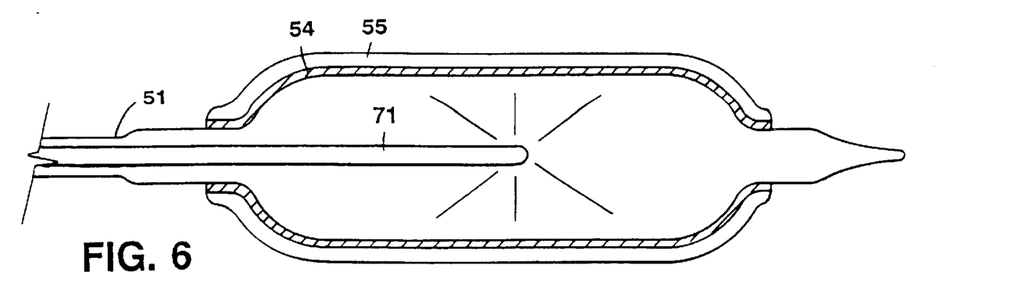
FIG. 6 is a cross sectional view of a drug delivery balloon catheter with an electromagnetic radiation-emitting fiber.

In addition to administering a solution containing a triggering agent to the hydrogel 55 to trigger drug release drug release is triggered by exposure of the hydrogel 55 to heat or light. As shown in FIG. 6, an electromagnetic radiation-emitting fiber 71 is inserted into the catheter 51 and extended into the balloon portion 54, where the emission of electromagnetic radiation, e.g., visible or ultraviolet light, from the fiber 71 contacts, e.g., illuminates, the hydrogel 55. The hydrogel 55 responds to the electromagnetic radiation by contracting as shown in FIG. 4 or swelling as shown in FIG. 5. Drug is then released from the contracted hydrogel 63 or expanded hydrogel 64, respectively.

Figure 7:
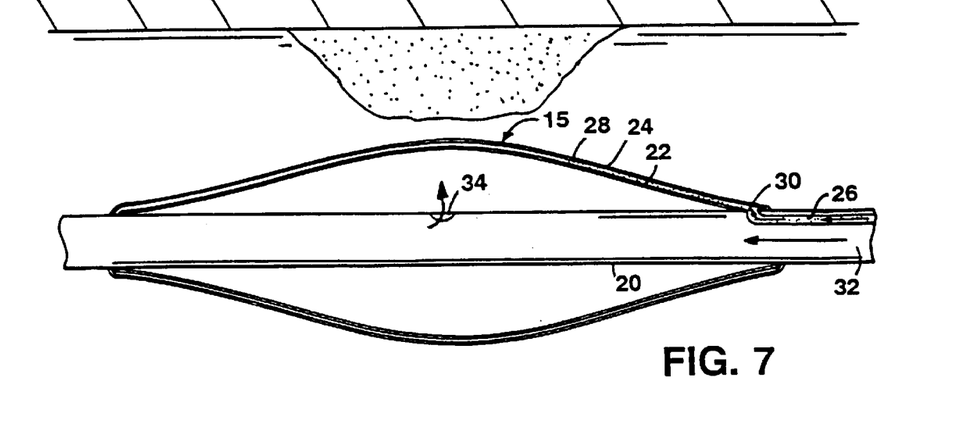
FIG. 7 is an enlarged, cross-sectional view of a drug delivery balloon catheter, including a semi-permeable outer balloon and an inner balloon.

Solutions carrying a triggering agent are delivered to a hydrogel coating on the outside of a balloon catheter using a double membrane catheter, as shown in FIG. 7. A catheter 20 carries an inner balloon 22 and an outer balloon 24, the latter including at least a portion formed of porous material 15 through which the a triggering agent or drug may pass to the hydrogel coating on the outer balloon under conditions of pressure. The outer balloon is coated with a hydrogel in which a drug is immobilized until released from the hydrogel by contacting the hydrogel with a solution containing a triggering agent. The triggering agent is introduced through a first lumen 26 into the intermediate region 28 between the balloons 22 and 24 via the first aperture 30. At the time of dilatation, inflation fluid passes through a second lumen 32 and through port 34 to inflate the inner balloon 22. Inflation of the inner balloon 22 provides the pressure needed on the solution in the intermediate region 28 to effect passage of the solution through openings of the membrane 15. The inner balloon 22 is deflated, and the intermediate region 28 refilled in order to repeat the process. After release of the drug from the hydrogel is triggered by the triggering agent, the balloon is deflated and the intermediate region 28 filled with drug which is then delivered to the hydrogel coating to replenish it. The process of replenishing the hydrogel with drug and delivering a triggering agent to the hydrogel to induce the release of drug from the hydrogel may be repeated as many times as desired.

Figure 7A:
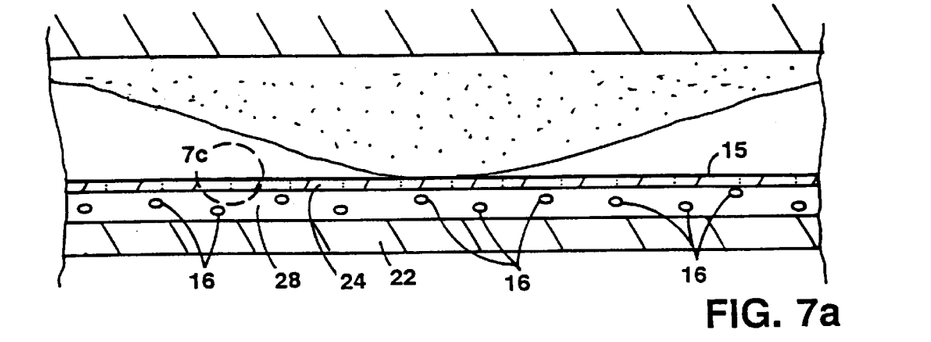
Figure 7B:
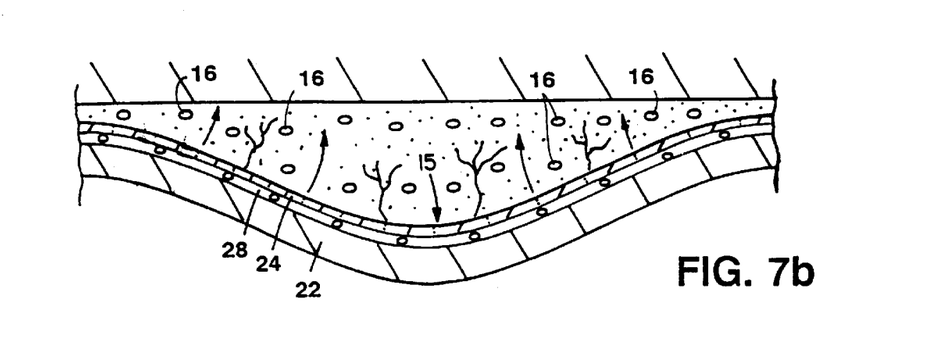
Figure 7C:
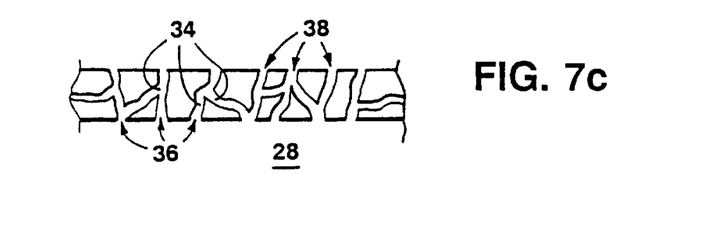
FIG. 7c is a much enlarged cross sectional view of the region C in FIG. 7a of the membrane, illustrating tortuous pathways through the thickness of the membrane.

The inner balloon may be of the type used in dilatation of blood vessels and made, for example, of a somewhat compliant material such as polyethylene that conforms to the shape of the body lumen wall or a nondistendable material such as PET. At least a portion of the outer balloon membrane may include a membrane selected such that the membrane creates sufficient resistance so that the triggering agent or drug weeps out of the membrane and into the hydrogel coating. This gentle application is advantageous since injury or disruption of the vessel wall is avoided. Preferably, the membrane has at least one layer of hydrophobic material having small openings, e.g., 2–20 microns, create a large pressure drop across the membrane to dissipate the pressure applied to the solution in the region 28 during balloon inflation and effect a low-energy weeping delivery of triggering agent or drug. Prior to pressuring the solution, the small openings prevent the flow of the solution from the region 28 (or the contamination of the region 28 with body fluid from the body lumen) as further discussed below. Referring to FIG. 7c, the membrane material 24 includes a series of tortuous paths 34 through its thickness connecting openings 36 on its inner surface exposed to the region 28 and openings 38 exposed to the body lumen. The flow of solution through the pathways reduces the velocity of the solution and enables gentle application to hydrogel and then to the tissue. Suitable materials include, but are not limited to, GORETEX® (an expanded porous fluorocarbon plastic material) and ultrahigh molecular weight microporous polyethylene (a polyethylene material available through Millipore, Inc. and commonly used for filter membranes).

Either the entire balloon 24 is formed from the semi-permeable material or a patch of the material is attached to a normal balloon e.g. by heat sealing. Other semi-permeable membranes may be formed by providing relatively large, substantially straight pathways through a hydrogel material and applying thereover, on the outside of the membrane, a hydrogel, e.g., of polyacrylic acid of the type described in U.S. Ser. No. 297,331, filed Jan. 17, 1989, the entire contents of which are incorporated herein by reference. Low energy application may also be achieved by a porous material formed of a series of layers having offset openings or a series of woven layers, which create a tortuous pathway for passage of a solution.

Preferably, the semi-permeable material is hydrophobic with openings of size selected to prevent substantial flow of solutions from the region 28 until sufficient pressure is applied. Referring to FIGS. 7a–7b, the water intrusion pressure of the permeable hydrophobic material and that of the solution are selected such that the solution will not normally pass through the openings unless sufficient pressure is applied by inner the balloon 22. Selection of the proper intrusion pressure for the semi-permeable material 15 of the outer balloon 24 prevents passage of the solution 16 through the openings of the material 15 when the balloon is less than fully inflated.

As demonstrated in FIG. 7b, under conditions of sufficiently high intrusion pressure (e.g., with the balloon fully inflated), the solution of triggering agent or drug 16 passes through the openings in a low-pressure, low-energy, non-injurious manner. The inner balloon 22 may be deflated, and the device may be refilled with triggering agent or drug, if necessary, and moved to various locations, where the inner balloon 22 is reinflated to deliver the triggering agent or drug, or a different concentration thereof, or another drug altogether to the various locations. This process may be repeated. A constant pressure pump may be used to maintain the balloon pressure above that needed to administer a solution through the openings during treatment. It will be understood that the amount of the triggering agent or drug delivered may also be carefully controlled by application of sufficient pressure to enable administration, then reducing the pressure below the threshold for passage through the openings, at which point, delivery of solution to the hydrogel ceases.

The procedure can be performed in many body lumens, most preferably, the vascular system in which case dilatation of a stenosed blood vessel may be carried out before, after or simultaneously with drug application.

Triggering Conditions

The drug to be administered to the patient can be loaded into the hydrogel, e.g., a hydrogel, coating in a variety of ways, e.g., by absorption, adding the drug into the prepolymers, coating the balloon with a drug-containing hydrogel, or chemically bonding the drug in or on the hydrogel, e.g., by covalent, ionic, or hydrogen bonding. To induce release of the drug from the hydrogel, solutions containing triggering agents are infused from the balloon portion of a catheter or from a space between the two membranes of the double membrane balloon catheter. Upon contact with a triggering agent, the hydrogel reacts, e.g., swells or contracts, such that the drug is delivered to the desired body tissue in a burst or over a desired time frame.

In addition to acting on the hydrogel itself, the triggering agents may act on the drug/hydrogen bond. For example, a triggering agent may change the nature of the microenvironment of the drug/hydrogel to render it incompatible with the drug/hydrogel interaction, e.g., by changing the ionic strength with a physiologically-acceptable salt solution or with a solution having a pH slightly above or below the pH optimum of the drug/hydrogel interaction. The pH of the triggering solution may be slightly above or below the pH of of the desired location of drug delivery. For example, drugs to be delivered to the bladder or intestine should be retained in the hydrogel under basic conditions and released from the hydrogel under acidic conditions.

In addition to a triggering drug release from a hydrogel by contacting the hydrogel with a solution containing one or more triggering agents, drug release may be induced by a change in a physical condition, e.g., heat, light, or pressure. Thermal catheters may be used to create a temperature change required to induce drug release, and catheters equipped with a fiber optic device can administer electromagnetic radiation, e.g., light of a specific wavelength, to trigger drug release from a photo-sensitive hydrogel-coated balloon. The hydrogel coating on the balloon is responsive to a change in physical or chemical changes, and the solutions which trigger release of the drug from the hydrogel mediate such physical or chemical changes, e.g., a change in ionic strength, pH, temperature, light or pressure.

EXAMPLE 1

Hydrogel-Coated Balloon Catheters Capable of Infusing Solutions Containing Triggering Agents Catheters, such as those with a porous balloon having pores or channels through which a solution, e.g., a solution containing a triggering agent, can pass, can be coated with a hydrogel which is responsive to a triggering agent, i.e., the hydrogel releases a drug when contacted with a triggering agent. A suitable channel balloon is discussed in Wang, U.S. Pat. No. 5,254,089, hereby incorporated by reference. Infusion catheters which have ports or openings adjacent to a balloon portion, i.e., upstream of the balloon portion relative to the direction of blood flow, can also be used to deliver the triggering agent to the drug/hydrogel coating on the balloon to trigger drug release. In this case, a solution containing a triggering agent would be administered from the ports and the blood flow within a blood vessel would wash the triggering agent over the surface of the drug/hydrogel coating, thus triggering drug release from the hydrogel to the adjacent tissue.

Porous balloons may also be used to replenish the dose of drug in the hydrogel, thus overcoming the limitation of drug quantity in the gel. For example, the hydrogel can be loaded with drug by passing it through the gel, where it becomes immobilized. The drug is then released from the hydrogel by infusion of the triggering solution into the gel. If an additional dose of drug is required, more drug could be infused into the gel from the balloon and the release process repeated.

A pressure-sensitive hydrogel coating may also be replenished in this manner. For example, after loading of a pressure-sensitive hydrogel coating with drug, inflation of the balloon against a passage wall, e.g., a blood vessel, at a certain pressure causes release of the drug. To replenish the pressure-sensitive hydrogel coating on the balloon, an additional dose of drug is infused into the hydrogel and the inflation-mediated release of drug repeated.

Hydrogel coatings on infusion wires, such as Katzen or Meiwessen infusion wires, may also be replenished with additional doses of drugs in this manner.

EXAMPLE 2

Thermal Catheters and Changes in Temperature as Triggering Condition

The expandable portion of a balloon catheter can be adapted for application of heat. Such a thermal catheter can be equipped with electrodes. Application of heat can trigger the release of drug from a hydrogel coating.

The drug is held within a hydrogel coating applied to the exterior of a thermal balloon. The balloon is positioned in the lumen in a region to be treated and inflated such that the hydrogel coating is in contact with the tissue. Heating of the balloon heats the drug-loaded hydrogel coating. The increase in temperature induces a volume phase transition, e.g., an expansion or contraction, of the gel, which triggers release of the drug from the hydrogel. The drug/hydrogel coating on the balloon portion of the catheter may also be heated using a fiber optic device as a local heat source.

Another suitable heated drug delivery catheter is discussed in Lennox et al. "Heated Balloon Catheters and the Like," U.S. Pat. No. 4,955,377, hereby incorporated by reference. Inflating liquid can be heated as a result of $I^2R$ losses by radiofrequency current flowing in the inflation fluid, e.g., saline, between electrodes, the liquid in turn heating the balloon wall.

Hydrogel formulations which undergo a volume phase transition in response to a temperature change may be nonionic or ionic poly(N-isopropylacrylamide) polymers and derivatives thereof. These hydrogels are typically swollen at low temperatures and collapse or shrink at higher temperatures, e.g., greater than about 34° C. Contraction of a drug-loaded hydrogel triggers drug release by squeezing the drug out of the hydrogel. Hydrogel polymers which swell when subjected to a temperature increase may also be used to trigger drug release. In this case, the drug diffuses out of the swollen hydrogel to the surrounding tissue. Varying the polymer composition can alter the temperature at which the volume phase transition occurs to optimize drug delivery to various locations in the body.

The temperature to which the responsive hydrogel is exposed as well as the rate of temperature increase or decrease may be used to control the rate of release of the drug from the hydrogel. The temperature increase may be 1–80° C. above body temperature of the patient, e.g., 37° C. for humans. The temperature chosen should avoid extensive damage to the surrounding tissue; little or no tissue damage was observed with temperature increases of 1–50° C. above body temperature. Optimally, the temperature increase to trigger drug release from a temperature-sensitive hydrogel is 1–5° C. above body temperature, e.g., 38–42° C.

EXAMPLE 3

Fiber-Optic Device-Equipped Catheters and Light as a Triggering Condition

The expandable portion of a balloon catheter can also be adapted for application of light of varying wavelengths. Such a catheter can be equipped with light source which can be controlled, i.e., by switching on or off or by altering the wavelength, to trigger release of a drug in a photo-sensitive hydrogel coating.

Volume phase transitions may be induced in certain photo-sensitive hydrogels. Such hydrogels may contain a photo-sensitive compound, e.g., a chromophore, which can absorb light of a specific wavelength and induce a charge transfer which may destabilize a drug/hydrogel interaction. Absorption of light by the chromophore may also be dissipated as heat, thus increasing the temperature of the hydrogel which in turn induces a volume phase change.

For example, N-propylacrylamide can be copolymerized with the chromophore, chlorophyllin (trisodium salt of copper chlorophyllin). This photo-sensitive polymer is swollen in the absence of light and collapses or shrinks when exposed to light of a visible wavelength. Drugs associated with this type of photo-sensitive hydrogel would be forced out of the hydrogel as contraction of the hydrogel is induced by exposure to a visible wavelength of light. Instead of chlorophyllin, other chromophores or light-sensitive dyes, e.g., rhodamine, may be incorporated into hydrogels to alter the behavior of the hydrogel upon exposure to light.

UV light can also be used to induce a volume phase transition in a drug-loaded hydrogel to trigger drug release. UV-sensitive compounds, such as leucocyanide or leucohydroxide or derivatives thereof, can be incorporated into a hydrogel. For example, photo-sensitive copolymer of N-isopropylacrylamide and bis (4-(dimethylamino)phenyl) (4-vinylphenyl)methyl leucocyanide, swells when exposed to UV light and contracts when the UV light is removed. Release of drugs associated with this type of gel can be triggered by switching the UV light source on and off. Alternatively, drug release can be controlled by exposing the hydrogel to two or more different wavelengths of light.

EXAMPLE 4

Drug Delivery Balloon Catheter with Inner Balloon and Semi-Permeable Hydrogel-Coated Outer Balloon Triggering solutions can also be administered to a responsive hydrogel using a double balloon-type catheter. The catheter is constructed for insertion in a body lumen and has a catheter shaft and an expandable balloon portion mounted on the catheter shaft. The expandable balloon portion is expandable to a controlled pressure to fill the cross section of the body lumen and press against the wall of the body lumen. At least a portion of the exterior surface of the expandable balloon portion is defined by a porous membrane which is coated with a hydrogel in which a drug is immobilized. The porous membrane is positioned over the surface of the balloon creating therebetween a space into which a triggering agent or a drug can be introduced. The porous membrane is formed of a select material and is constructed to release a solution from the space through openings in the membrane to the outer surface of the membrane in a noninjurious low pressure manner. The application of drug or triggering agent occurs in response to pressure applied by inflation of the balloon to compress the space.

The catheter may include one or more of the following features. The porous membrane has a series of tortuous pathways through its thickness between openings exposed to the space between the two membranes and openings exposed to the hydrogel coating and/or the body lumen. The openings are of selected small size to prevent the flow of fluid prior to the application of pressure to the solution in the space. The drug or triggering agent is in an aqueous solution and the porous material is a hydrophobic material. The openings are in the range of about 2 to 20 $\mu$m. The membrane material is selected from the group consisting of porous fluorocarbon plastic material and ultrahigh molecular weight microporous polyethylene. The membrane comprises a plurality of layers of material, the orifice of which collectively define the tortuous pathways.

The method includes preparing the balloon portion by introducing an aqueous solution of the triggering agent to the space, introducing the catheter to the body lumen to position the expandable portion at the point of desired drug application, and expanding the expandable balloon portion to enable delivery of the triggering agent to the drug-laden hydrogel by compression of the space. The method further comprises, deflating the balloon and repeating the preparing and expanding steps. The method may also include a drug replenishment step in which after the drug is released from the hydrogel.

Other embodiments are within the claims.

What is claimed is:

1. A method for delivering a drug to tissue at a desired location within the body, comprising:

providing a drug substantially immobilized in a hydrogel;

providing a solution comprising a triggering agent that differs from ambient physiological conditions;

providing a catheter constructed for insertion in the body, a portion of said catheter carrying said hydrogel with a predetermined substantial amount of said drug incorporated therein;

introducing said catheter to the body at the point of desired drug application; and exposing said hydrogel to said triggering agent.

2. The method of claim 1, wherein exposing said hydrogel to said triggering agent increases local ionic strength, thereby triggering release of said drug from said hydrogel.

3. The method of claim 2, wherein said drug is associated with said hydrogel by an ionic interaction and exposing said hydrogel to said triggering agent disrupts said ionic interaction.

4. The method of claim 3, wherein said triggering agent is a saline solution having a molarity of at least 0.2 molar.

5. The method of claim 3, wherein said drug is cationic and said hydrogel is anionic.

6. The method of claim 3, wherein said drug is anionic and said hydrogel is cationic.

7. The method of claim 1, wherein said triggering agent is a solution with a pH that induces a volume phase transition of said hydrogel, thereby triggering release of said drug.

8. The method of claim 6, wherein said solution has a pH of greater than about 7.5.

9. The method of claim 6, wherein said solution has a pH of less than about 7.3.

10. The method of claim 1, wherein said drug is an anti-proliferative drug.

11. The method of claim 1, wherein said drug is an anti-thrombogenic drug.

12. The method of claim 1, wherein said drug is a thrombolytic drug.

13. A method for triggering release of a drug from a hydrogel to a tissue at a desired location of a wall of a body lumen, comprising:

providing a drug substantially immobilized in a hydrogel;

providing a solution comprising a triggering agent that differs from ambient physiological conditions;

providing a catheter constructed for insertion in a body lumen having a catheter shaft with an expandable balloon portion mounted on said catheter shaft;

said balloon portion being expandable to engage the tissue at a controlled pressure to fill a cross-section of the body lumen and press against the wall of the body lumen;

said balloon portion being coated on its outer surface with said hydrogel;

introducing said catheter to the body lumen wherein said balloon portion is positioned at the point of desired drug application;

expanding said balloon portion to engage the tissue; and exposing said hydrogel to said triggering agent.

14. A method for delivering a drug to tissue at a desired location within the body, comprising:

provi ding a drug substantially immobilized in a hydrogel, wherein said hydrogel is a photo-sensitive polymer comprising a photosensitive compound;

providing a catheter constructed for insertion in the body, a portion of said catheter carrying said hydrogel having the capacity to incorporate a predetermined substantial amount of said drug;

introducing said catheter to the body at the point of desired drug application; and illuminating said hydrogel with visible or ultraviolet light.

15. The method of claim 14, wherein said photosensitive compound comprises a porphyrin ring.

16. The method of claim 14, wherein said photosensitive compound is selected from the group consisting of rhodamine, chlorophyllin, leucocyanide, and leucohydroxide.

* * * * *